US012680134B2

(12) United States Patent
Holme et al.

(10) Patent No.: US 12,680,134 B2
(45) Date of Patent: Jul. 14, 2026

(54) METHOD FOR DETECTING A NUCLEIC ACID SEQUENCE

(71) Applicant: 3CR Bioscience Ltd., Harlow (GB)

(72) Inventors: John Holme, Harlow (GB); Nisha Jain, Harlow (GB); Steven Asquith, Harlow (GB)

(73) Assignee: 3CR Bioscience Ltd., Harlow (GB)

( * ) Notice: Subject to any disclaimer, the term of this patent is extended or adjusted under 35 U.S.C. 154(b) by 166 days.

(21) Appl. No.: 17/309,998

(22) PCT Filed: Jan. 9, 2020

(86) PCT No.: PCT/GB2020/050040
§ 371 (c)(1),
(2) Date: Jul. 8, 2021

(87) PCT Pub. No.: WO2020/144480
PCT Pub. Date: Jul. 16, 2020

(65) Prior Publication Data
US 2022/0090194 A1    Mar. 24, 2022

(30) Foreign Application Priority Data

Jan. 9, 2019    (GB) ...................................... 1900311
Jan. 9, 2019    (GB) ...................................... 1900312

(51) Int. Cl.
*C12Q 1/6876*    (2018.01)
*C12N 9/12*    (2006.01)

(52) U.S. Cl.
CPC ......... *C12Q 1/6876* (2013.01); *C12N 9/1252* (2013.01); *C12Y 207/07007* (2013.01); *C12Q 2600/156* (2013.01)

(58) Field of Classification Search
USPC ......... 435/6.1, 6.11, 6.12, 91.1, 91.2, 91.51; 436/94, 501; 536/23.1, 24.3, 24.33, 25.3
See application file for complete search history.

(56) References Cited

U.S. PATENT DOCUMENTS

| | | | | |
|---|---|---|---|---|
| 6,103,476 | A * | 8/2000 | Tyagi ................... | C12Q 1/6827 435/6.1 |
| 6,183,997 | B1 * | 2/2001 | Hogrefe ................... | C12N 9/16 536/23.7 |
| 6,270,967 | B1 | 8/2001 | Whitcombe et al. | |
| 2002/0090633 | A1 * | 7/2002 | Becker ................. | C12Q 1/6818 435/6.12 |
| 2006/0141518 | A1 | 6/2006 | Lao et al. | |
| 2013/0288245 | A1 * | 10/2013 | Walder ................. | C12N 9/1252 435/199 |
| 2014/0370506 | A1 * | 12/2014 | Carlson ................ | C12Q 1/6816 536/24.3 |

FOREIGN PATENT DOCUMENTS

| | | |
|---|---|---|
| EP | 1726664 B1 | 1/2010 |
| GB | 2526445 A | 11/2015 |
| JP | 2017/131164 A | 8/2017 |
| WO | 2005/113829 A2 | 12/2005 |
| WO | 2010/062776 A2 | 6/2010 |
| WO | 2016/172632 A2 | 10/2016 |

OTHER PUBLICATIONS

Baskaran et al: "Uniform amplification of a mixture of deoxyribonucleic acids with varying GC content", PCR Methods & Applications, vol. 6, No. 7, Jul. 1, 1996 (Jul. 1, 1996), pp. 633-638, Cold Spring Harbor Laboratory Press, US.

Faltin et al: "Current Methods for Fluorescence-Based Universal Sequence-Dependent Detection of Nucleic Acids in Homogenous Assays and Clinical Applications", Clinical Chemistry, P.B. Hoeber, vol. 59, No. 11, Nov. 1, 2013 (Nov. 1, 2013), pp. 1567-1582.

He, Zhili et al: "Empirical establishment of oligonucleotide probe design criteria", Applied and Environmental Microbiology, vol. 71, No. 7, Jul. 1, 2005 (Jul. 1, 2005), pp. 3753-3760, American Society for Microbiology, US.

Omni Klentaq Enables Direct DNA Amplification Inhibition Resistant, High Performance, Hot-Start Taq DNA Polymerase, Jan. 1, 2011 (Jan. 1, 2011), XP055620642, Retrieved from the Internet:URL:http://enzymatics.com/pdf/Ultra-Pure Omni-Klentaq. pdf.

PCT International Preliminary Report on Patentability issued in International Application No. PCT/GB2020/050040, dated Jun. 16, 2021.

* cited by examiner

*Primary Examiner* — Anne M. Gussow
(74) *Attorney, Agent, or Firm* — Bochner PLLC; Beverly W. Lubit

(57)    ABSTRACT

The present invention relates to a method for detecting one or more target sequences in a sample by amplification. Kits and compositions for use with the method are also provided.

24 Claims, 9 Drawing Sheets
Specification includes a Sequence Listing.

FIGURE 1
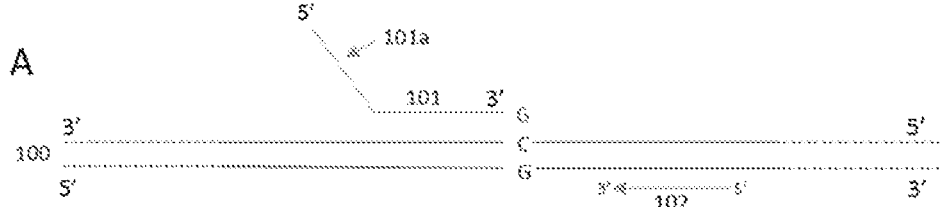
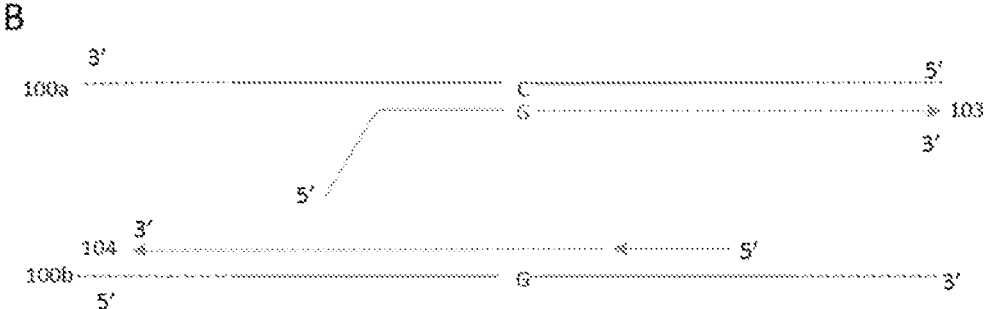
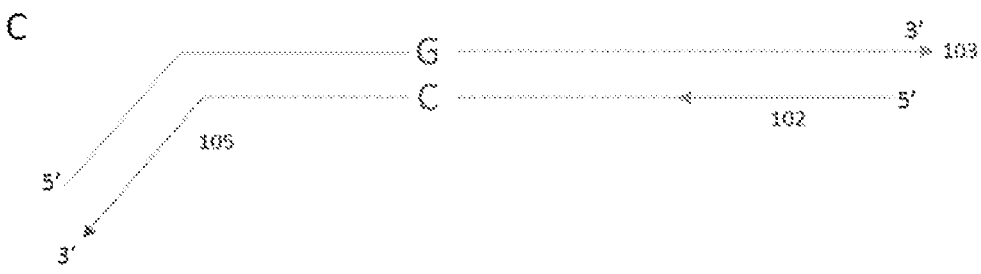
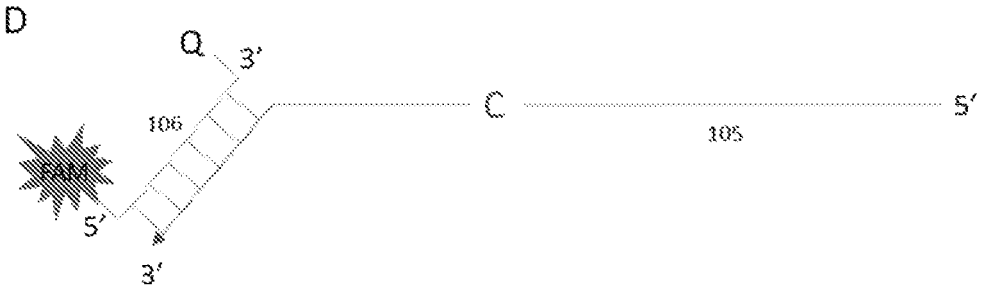

FIGURE 8

Fluorescent probe 1

/56-FAM/AGCTGCTATTGTTACCAGTGACGCAGCT/3IABkFQ/

```
        56-FAM AGCTGC TATTGT ⟶
               ||||||        ᴬᶜ
        3IABkFQ TCGACG CACTAG ⟵ ꜀
```

Fluorescent probe 2

/5HEX/TGGCCAGTGTATTCTGCACAGGTGGCCA/3IABkFQ/

```
        5HEX TGGCCA GTGTAT ⟶
              ||||||        ᶜᵀ
       3IABkFQ ACCGGT CACAGG ⟵ ᵍ
```

Enhancer Primer 1

GCTGCTATTGTTACCAGTGACGCAGCT

```
        GCTGC TATTGT ⟶
              |||||        ᴬᶜ
        CGACG CACTAG ⟵ ꜀
```

Enhancer Primer 2

GGCCAGTGTATTCTGCACAGGTGGCCA

```
        GGCCA GTGTAT ⟶
              |||||        ᶜᵀ
        CCGGT CACAGG ⟵ ᵍ
```

METHOD FOR DETECTING A NUCLEIC ACID SEQUENCE

CROSS-REFERENCE TO RELATED APPLICATIONS

This application is a national phase application under 35 U.S.C. § 371 that claims priority to International Application No. PCT/GB2020/050040 filed Jan. 8, 2020, which claims priority to both United Kingdom Patent Application No. 1900311.0 filed Jan. 9, 2019 and United Kingdom Patent Application No. 1900312.8 filed Jan. 9, 2019, all of which are incorporated herein by reference in their entirety.

The instant application contains a Sequence Listing which has been submitted in txt format and is hereby incorporated by reference in its entirety. Said txt copy, created on Feb. 26, 2024, is named "P41484US-pct2020050040-seql_Updated26_ 2_24_ST25" and is 6K bytes in size.

FIELD OF THE INVENTION

The present invention relates to methods and kits for nucleic acid detection and/or amplification, such as in an assay system.

BACKGROUND OF THE INVENTION

Advancements in molecular biology techniques, in particular the polymerase chain reaction (PCR) has enabled the development of processes which enable a greater understanding of an individual's genetic make-up (i.e. their genotype).

Genotyping is a generic term given to various nucleic acid analysis techniques that identify alterations or polymorphisms within known sequences, and usually for a given individual. These techniques are useful in many aspects of scientific, medical and forensic fields. For example, these techniques can be used to examine particular genetic loci in an individual in order to diagnose hereditary diseases or provide prognosis based on known genetic lesions. Particular modifications of interest include, for example, point mutations, deletions, insertions and inversions as well as polymorphisms within nucleic acid sequences of interest. These techniques can also be used for clinical purposes such as tissue typing for histocompatibility or for forensic purposes such as identity or paternity determination.

In many PCR based genotyping reactions, a signal producing system is employed to detect the production of amplified product. One type of signal producing system that is commonly used is the fluorescence energy transfer (FRET) system, in which a nucleic acid detector includes fluorescence donor and acceptor groups (see, for example, European Patent 1726664). A primary consideration with PCR-based techniques that employ a FRET-based system is that the signal generated must be highly specific and sensitive to ensure accurate results. High fidelity amplification is also critical.

Thus, there is a continuing need to improve both the sensitivity and accuracy of PCR-based genotyping systems.

SUMMARY OF THE INVENTION

In one aspect, the present invention provides a method for detecting (and/or amplifying) one or more (target) sequences (e.g. in a sample), such as by amplification, the method comprising:

a) providing an aqueous composition comprising:
   i) one or more (forward) oligonucleotide primers (each) having a 5' region which is a tag sequence and a 3' region specific for a target sequence;
   ii) a (reverse) oligonucleotide primer, such that a forward and the reverse primer may operably form a primer pair;
   iii) one or more probe(s) (each) having a reporter (label) and a quencher (label), each probe suitably comprising a sequence having at least 50% identity e.g. to the tag sequence of a (forward) oligonucleotide primer; and
   iv) one or more (enhancer) oligonucleotide primer(s) comprising a sequence having at least 50% identity e.g. to the sequence of a probe;
b) suitably, incubating the primers and probes with the sample and at least one polymerase; and
c) suitably, performing polymerase chain reaction (PCR) e.g. on the sample, for example to generate tagged nucleic acids, optionally whereby the probe(s) can bind the tagged nucleic acids.

In another aspect, the present invention also provides a kit suitable for use in a (nucleic acid amplification) method or process, comprising:
   i) one or more (forward) oligonucleotide primer(s) (each) having a 5' region which is a tag sequence and a 3' region specific for a target sequence;
   ii) a (reverse) oligonucleotide primer, such that a forward and the reverse primer may operably form a primer pair;
   iii) one or more probe(s) (each) having a reporter (label) and a quencher (label), each probe suitably comprising a sequence having at least 50% identity e.g. to the tag sequence of a forward oligonucleotide primer;
   iv) one or more (enhancer) oligonucleotide primers comprising a sequence having at least 50% identity to the sequence of a probe; and
   v) optionally, a polymerase.

In some embodiments, the reporter (label) may be located on or at a different portion of the probe compared to the quencher (label). The position of the labels maybe such that (e.g. when free in solution), the reporter (label) and quencher (label) may come into close proximity to each other such that the reporter is (at least partially) quenched, or little or no emission can be emitted and/or detected from the reporter (label).

Preferably the polymerase is a DNA polymerase, for example, a fragment or domain or a derivative of (Taq) polymerase. In some embodiments, the polymerase is a modified polymerase. In some embodiments, the polymerase is modified to reduce and/or remove exo-nuclease activity and/or modified to be a "hot-start" polymerase.

The one or more (enhancer) oligonucleotide primer(s) may comprise at least two (distinct) regions. Each region can comprise a sequence having at least 50% identity, such as to one or more probe(s). The two distinct regions may be separated, e.g. by a linker region. The linker region may be 2 to 5 or 10 oligonucleotides in length. In some embodiments, there may be no linker region.

Suitably the one or more probe(s) may comprise a sequence having at least 60%, 70%, 80%, 90%, 95%, 98% or 99% identity, such as to the tag sequence of a (forward) oligonucleotide primer. In some embodiments, the one or more probe(s) comprise a sequence identical to the tag sequence of a (forward) oligonucleotide primer.

The one or more (enhancer) oligonucleotide primer(s) can comprise a sequence having at least 60%, 70%, 80%, 90%, 95%, 98% or 99% identity e.g. to the sequence of a probe. In some embodiments, the one or more enhancer oligonucleotide primer(s) comprise a sequence identical to the sequence of a probe.

Suitably, the one or more probes may comprise a hairpin or loop structure. Suitably, the one or more probes may comprise a portion at or adjacent to the 3' terminus which is complementary to a portion at or adjacent to the 5' terminus. In some embodiments, the 3' terminal portion and/or the 5' terminal portion have a length of at least 4, at least 5, at least 6 or at least 7 nucleotides. In some embodiments, the 3' terminal portion and the 5' terminal portion have at least 50%, at least 60%, at least 70%, at least 80%, or at least 90% complementarity. In some embodiments, the 3' terminal portion and the 5' terminal portion have 100% complementarity.

Suitably, the one or more enhancer oligonucleotide primers may comprise a hairpin or loop structure. Suitably, the one or more enhancer oligonucleotide primers may comprise a portion at or adjacent to the 3' terminus which is complementary to a portion at or adjacent to the 5' terminus. In some embodiments, the 3' terminal portion and/or the 5' terminal portion have a length of at least 4, at least 5, at least 6 or at least 7 nucleotides. In some embodiments, the 3' terminal portion and the 5' terminal portion have at least 50%, at least 60%, at least 70%, at least 80%, or at least 90% complementarity. In some embodiments, the 3' terminal portion and the 5' terminal portion have 100% complementarity. In some embodiments, the 3' terminal portion and the 5' terminal portion comprises one, two or three mismatches. In some embodiments, the 3' terminus or the 5' terminus further comprises an overhang portion of one, two or three nucleotides which does not hybridize to a complementary nucleotide on the 5' or 3' terminal portion respectively.

Suitably, the one or more enhancer oligonucleotide primers may be configured such that the hairpin structure in the one or more enhancer oligonucleotide primers is less stable than the hairpin structure in the one or more probes.

In some embodiments of the methods, at least 4, 10, 15, 20, 25 or 30 cycles of PCR are performed. In some embodiments, up to/no more than 35, 40, 45 or 50 cycles of PCR are performed.

In some embodiments the method may further comprise:

d) detecting or measuring the signal generated by the binding of the probes to the (tagged) nucleic acid(s). The measurement may be made in real time and/or at the end of the reaction.

In some embodiments of the methods and kits as provided herein, the composition or kit further comprises a quaternary ammonium salt.

Another aspect of the present invention provides the use of a quaternary ammonium salt (or source thereof) in a method as provided herein. It may have the formula $N(Alk)_x$ $H_y$, Hal, $N(Alk)_xH_y$ where x+y=4, Alk=C1-4 alkyl, and Hal=halide.

The quaternary ammonium salt (QAS) may be a halide (e.g. chloride) salt. The quaternary ammonium salt may comprise 1-4 methyl groups. Suitably, the quaternary ammonium salt may comprise a tetramethylammonium salt; preferably the tetramethylammonium salt is tetramethylammonium chloride (TMAC). In some embodiments, the presence of TMAC can increase the signal-to-noise ratio of the signal from the probe(s).

In another aspect, the present invention provides a modified polymerase with reduced or no exonuclease (herein abbreviated to P-ENF) function or activity for use in a nucleic acid amplification method or process, e.g. a DNA amplification method.

The polymerase may a fragment and/or domain and/or a derivative of Taq polymerase.

The polymerase may be formed by an N-terminal truncation or modification.

The polymerase may be further modified to be a "hot-start" polymerase.

In another aspect, the present invention provides a method of conducting nucleic acid amplification using a P-ENF.

In another aspect, the present invention provides an aqueous composition suitable for nucleic acid amplification comprising one or more of:

a) a buffer;

b) dNTPs, which may comprise deoxyribonucleotide triphosphates (A, T, G and C);

c) a polymerase, such as a P-ENF as defined herein;

d) optionally, a (forward) primer and a (reverse) primer, preferably wherein the primers form a primer pair and/or are suitable for amplifying a target nucleic acid;

e) preferably, a quaternary ammonium salt (QAS, for example as defined earlier); and/or e) a source of divalent cations.

Such compositions may be suitable for amplifying DNA, for example in a polymerase chain reaction (PCR).

The QAS and/or P-ENF may be used in a method or composition comprising one or more probes with a reporter and/or quencher, or with at least 50% identity (to a primer), or one or more enhanced primer(s).

Also provided is a kit suitable for performing nucleic acid amplification comprising:

a) a container;

b) a P-ENF and/or a quaternary ammonium salt (QAS), suitably in an aqueous composition as defined herein.

BRIEF DESCRIPTION OF THE FIGURES

These are provided for illustration and are not intended to be limiting.

FIG. 1—Schematic of the UPDS methods as employed herein.

FIG. 8—Four nucleotide sequences as follows:

```
Fluorescent Probe 1:
                             (SEQ ID NO: 21)
5'-/56-FAM/AGCTGCTATTGTTACCAGTGACGCAGCT/3IABKFQ/-
3'

Fluorescent Probe 2:
                             (SEQ ID NO: 22)
5'-/5HEX/TGGCCAGTGTATTCTGCACAGGTGGCCA/3IABKFQ/-3'

Enhancer Primer 1:
                             (SEQ ID NO: 23)
5'-GCTGCTATTGTTACCAGTGACGCAGCT-3'

Enhancer Primer 2:
                             (SEQ ID NO: 24)
5'-GGCCAGTGTATTCTGCACAGGTGGCCA-3'
```

Figure 9A:
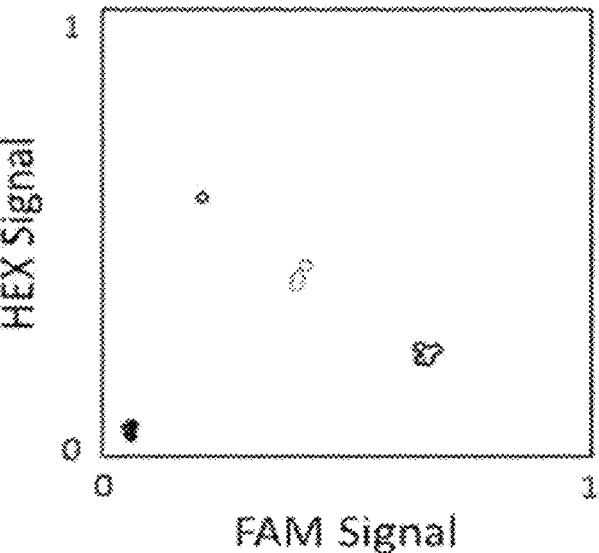
Figure 9B:
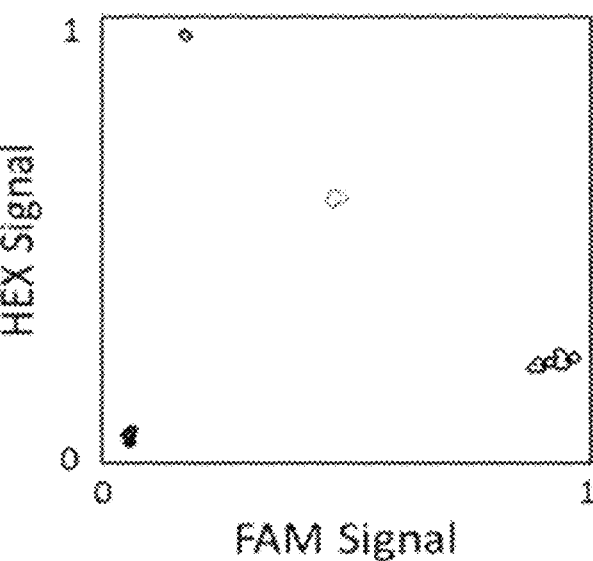

FIG. 9A and FIG. 9B show data from a genotyping assay using human genomic DNA. FIG. 9A shows a plot of FAM signal divided by ROX on the X axis generated with standard probes and enhancer primer (no self-complementary ends) targeting a SNP. FIG. 9B shows a plot of FAM signal divided by ROX on the X axis and HEX signal divided by ROX on the Y axis targeting the same SNP.

DETAILED DESCRIPTION

These aspects relate to a new genotyping method, disclosed herein as UPDS (Universal polymorphism detection system). This assay may comprise the use of two (or more, for example, three or four or five or more) competing allele-specific oligonucleotide primers. Each may comprise a portion of template sequence at the 3' end (which may differentiate between the alleles) and different non-template sequence tails, or tags, to the 5' end, and a (common) reverse primer. This system can use a reporting system, such as a fluorescent reporting system. This system may use a probe, such as an oligonucleotide probe. This system can then bind to the complementary sequence introduced by each of the tails of the allele-specific primers, leading to generation of detectable signal, such as a light signal.

A schematic of an exemplary UPDS process is shown in FIG. 1. In step (A), the correct allele specific primer 101 (only one shown for simplicity) with tail/tag 101a and reverse primer 102 are shown alongside the template DNA 100, showing the single nucleotide polymorphism (SNP) which exemplifies the specific allele (here it is a C-G). Following denaturation (into single stranded templates 100a and 100b), the primers anneal and extend, and step (B)

shows the resulting synthesis of two new strands 103 and 104. One of these strands 103 is tailed/tagged as a result of the use of the allele-specific primer, and subsequent extension steps—for example step (C)—causes synthesis of a strand comprising the complement of the allele-specific primer tail/tag 105. In step (D), this shows that the generation of the complement of the allele-specific tail/tag allows a probe such as the exemplified dual-labelled probe 106 (with a FAM fluorophore and a quencher) to bind/base-pair to the tail/tag portion and generate a detectable signal.

Figure 2:
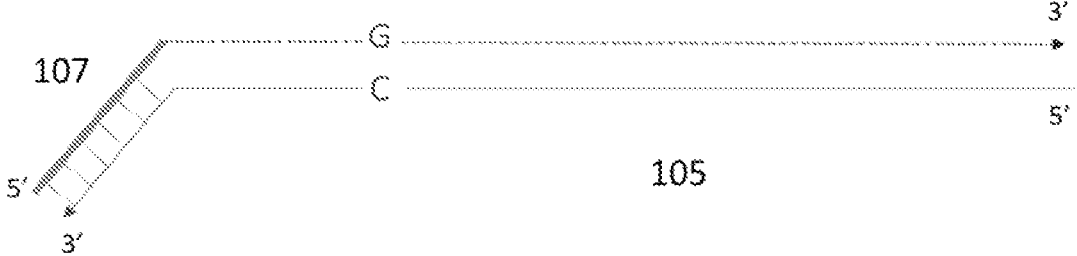
FIG. 2—Schematic of the enhancer primer mechanism in UPDS.

The action of the enhancer primer in the UPDS process is shown in FIG. 2. Here, following step (C) from FIG. 1, the enhancer primer 107 is able to compete with the probe for binding to the allele-specific tail/tag of synthesised strand 105. This allows for further rounds of amplification to generate further strands 105 resulting in a greater number of probe binding sites.

Thus in one aspect, the present invention provides a method for detecting one or more target sequences in a sample by amplification, the method comprising:

a) providing an aqueous composition comprising:
  i) one or more forward oligonucleotide primers having a 5' region which is a tag sequence and a 3' region specific for a target sequence;
  ii) a reverse oligonucleotide primer, such that a forward and the reverse primer operably form a primer pair;
  iii) one or more probes having a reporter label and a quencher label, each probe comprising a sequence having at least 50% identity to the tag sequence of a forward oligonucleotide primer; and
  iv) one or more enhancer oligonucleotide primers comprising a sequence having at least 50% identity to the sequence of a probe;
b) incubating the primers and probes with the sample and at least a polymerase; and
c) performing polymerase chain reaction (PCR) on the sample to generate tagged nucleic acids, whereby the probe(s) can bind the tagged nucleic acids.

The present invention also provides a kit for use in a nucleic acid amplification process, comprising:

i) one or more forward oligonucleotide primers having a 5' region which is a tag sequence and a 3' region specific for a target sequence;
ii) a reverse oligonucleotide primer, such that a forward and the reverse primer operably form a primer pair;
iii) one or more probes having a reporter label and a quencher label, each probe comprising a sequence having at least 50% identity to the tag sequence of a forward oligonucleotide primer;
iv) one or more enhancer oligonucleotide primers comprising a sequence having at least 50% identity to the sequence of a probe; and
v) a polymerase.

The term "sample" as used herein should be understood to mean a sample comprising or consisting of DNA. Generally, the sample may be a biological sample, for example a biological fluid selected from blood or a blood derived product such as plasma or serum, saliva, urine, sweat, or cerebrospinal fluid. The sample may also be a sample of cells or tissue, for example muscle, nail, hair, bone, marrow, brain, vascular tissue, kidney, liver, peripheral nerve tissue, skin and epithelial tissue. The tissue or cells may be normal or pathological tissue. Generally, the sample may be treated to remove all material except DNA by techniques well known in the art. PCR sample preparation protocols are also well described in the literature and are available from the websites of Agilent, Life Technologies, Qiagen and Illumina. In one embodiment, the method of the invention may be employed to determine the presence of a particular allele of a DNA locus, for example the presence of a SNP in a gene or other locus in DNA. In some embodiments, the sample comprises DNA of unknown origin and the method of the invention may be employed to detect the presence of a target DNA in the sample. The DNA present in a sample may be referred to as the DNA template in the context of the present disclosure.

The term "primer" as used herein refers to a synthetically or biologically produced single-stranded oligonucleotide. In use, primers can typically base pair/anneal to another single-stranded nucleic acid molecule using the rules defined by Watson-Crick base pairing to form a double-stranded nucleic acid duplex, whereby the primer strand can then be extended/elongated with an appropriate polymerase in the presence of nucleotide monomers. It is well known that many such nucleic acid polymerases or reverse transcriptases require the presence of a primer that may be extended to initiate such nucleic acid synthesis. For example, the oligonucleotides disclosed herein may be used as one or more primers in various extension, synthesis, or amplification reactions. It is also well known that in PCR assays, primers usually exist in primer pairs, which comprises of a nominal "forward" primer and a nominal "reverse" primer. Forward and reverse primers may be differentiated by the fact that they bind to different strands of a given duplex template, and operably form a primer pair such that the reverse primer binds downstream to the forward primer on the DNA duplex/template (i.e. in the 3' direction of the forward primer).

The term "portion" as used herein with reference to oligonucleotide constructs (such as primers) should be understood to mean a contiguous part of said oligonucleotide construct which comprises at least one, two, three, four, five or six or more contiguous bases.

In some embodiments, primers may have at least one portion which is specific for a target sequence (i.e. a sequence-specific primer). In other words, primers may be designed in such a way that at least one portion will have a sequence which is complementary to a target known sequence which is to be detected. Thus, in a given amplification reaction, a sequence-specific primer will preferentially base-pair/anneal to its target sequence.

Sequence-specific primers may also be allele-specific primers whereby the target sequence is a specific allele at a genetic locus which can be used to alleles that share a common polymorphism. The term "allele" as used herein refers to a genetic variation associated with a gene or a segment of DNA, i.e. one of two or more alternate forms of a DNA sequence occupying the same genetic locus. In other words, allele-specific primers may be used to amplify a single allele and may be capable of differentiating between two sequences that differ by only a single base difference of change. The difference between the two alleles may be a SNP, an insertion, or a deletion.

Sequence-specific primers may be universal for all alleles. In other words, sequence-specific primers may only be specific for a locus which is universal for all alleles and/or polymorphisms to be detected. These primers can therefore be used as universal primers. In other words, one universal sequence-specific primer can be used in conjunction with two or more allele-specific primers in a method of the invention as described herein. Thus, in one embodiment of the method of the invention, the one or more forward oligonucleotide primers may be allele-specific primers which have a sequence-specific portion which is specific for one or more known allele(s). In such embodiments, the reverse oligonucleotide primers may be sequence-specific primers specific for a known sequence near the allele. In one example, the sequence bound by the reverse primer is known to not be polymorphic and/or not be allele dependent.

Sequence-specific and/or allele-specific primers may also comprise a 5' portion which is a tag sequence, wherein tag sequence is not complementary to the target sequence or allele. This organisation allows for a tag sequence to be incorporated as part of the primer during a specific polymerisation reaction. Subsequent cycles during a PCR reaction will then allow the tag sequence to be amplified further and become incorporated as part of the amplified duplex. Tag sequences may be useful as they can be designed to be specific for complementary probe sequences, whereby the probes can be labelled using a reporter label to allow for the generation of an associated signal in response to amplification from a sequence-specific and/or allele-specific primer.

In some embodiments, the sequence of the sequence-specific portion of target-specific primers as used herein, such as allele-specific primers, can be designed such they are at least 50%, 60%, 70%, 80%, 85%, 90%, 95%, 96%, 97%, 98%, 99% or 100% identity to their target sequences (for example, a sequence comprising a SNP). In some embodiments, the sequence identity may be sufficient such that the target-specific primer is able to bind to the target sequence and allow for extension by the polymerase, for example the DNA polymerase, as part of the methods as provided herein. In some embodiments, the sequence identity is sufficient such that the target-specific primer is able to bind to the target sequence preferentially to the other target-specific primers which are present in the composition and/or kit.

Enhancer primers as used herein refer to sequence-specific primers which are specific for the same locus as a probe as used herein. Thus, in use, the enhancer primer may be able to compete with e.g. a probe in hybridizing, under defined stringencies, specifically (i.e., preferentially) to target nucleic acid sequences. The binding of the enhancer primer may facilitate the amplification reaction and thus generate further tagged/tailed strands for probe binding and signal generation. Thus, in embodiments, the one or more enhancer oligonucleotide primers comprise a sequence having at least 50% identity to the sequence of a probe. In some embodiments, the sequence of the oligonucleotide enhancer primers as used herein can be designed such they are at least 60%, 70%, 80%, 85%, 90%, 95%, 96%, 97%, 98%, 99% or 100% identity to their respective probe/tag sequences. In some embodiments, the sequence identity between the enhancer primer and the probe sequence may be sufficient such that the enhancer primer is able to bind or hybridize to the complementary tag sequence and allow for extension by the polymerase, for example the DNA polymerase, as part of the methods as provided herein. In some embodiments, the sequence having at least 50% identity to the sequence of a probe may be 10-30 nucleotides in length. In some embodiments, the sequence having at least 50% identity to the sequence of a probe may be 12-28, 15-27, 17-25, 19-23, 20-22 or 21 nucleotides in length. In some embodiments, the sequence having at least 50% identity to the sequence of a probe may be 10, 11, 12, 13, 14, 15, 16, 17, 18, 19, 20, 21, 22, 23, 24, 25, 26, 27, 28, 29 or 30 nucleotides in length. In some embodiments the one or more enhancer oligonucleotides may have the same length (in nucleotides) as the probe.

In some embodiments, the one or more enhancer oligonucleotide primers may comprise at least two distinct regions, each region comprising a sequence having at least 50% identity (or at least 60%, 70%, 80%, 85%, 90%, 95%, 96%, 97%, 98%, 99% or 100% identity) to that of the one or more probes. In some embodiments, the sequence identity between the each distinct region and the probe sequence may be sufficient such that the enhancer primer is able to bind or hybridize to the tag sequence and allow for extension by the polymerase, for example the DNA polymerase, as part of the methods as provided herein. In such embodiments, the two distinct regions may be separated by a linker region. The linker region may be 1 to 10 or 2 to 5 oligo-nucleotides in length. In some embodiments, there may be no linker region. In some embodiments, the sequence of each distinct region may be identical to each other.

In some embodiments, the one or more enhancer oligo-nucleotide primers may comprise a loop or hairpin structure. In such embodiments, the one or more enhancer oligonucle-otide primers may comprise a portion at or adjacent to the 3' terminus (the 3' terminal portion) which is complementary to a portion at or adjacent to the 5' terminus (the 5' terminal portion). In free solution, the 3' terminal portion can hybrid-ize to the 5' terminal portion and thus form a hairpin or loop structure. In some embodiments, the 3' terminal portion and the 5' terminal portion have a length of at least 4, at least 5, at least 6 or at least 7 nucleotides. In some embodiments, the 3' terminal portion and the 5' terminal portion have a length of 4-8, 5-7 or 6 nucleotides. In some embodiments, the 3' terminal portion and the 5' terminal portion have a length of 4, 5, 6, 7 or 8 nucleotides. In some embodiments, the 3' terminal portion and the 5' terminal portion have at least 50%, at least 60%, at least 70%, at least 80%, or at least 90% complementarity. In some embodiments, the 3' terminal portion and the 5' terminal portion have 100% complemen-tarity. In other embodiments, the 3' terminal portion and the 5' terminal portion has one, two or three mismatches. In some embodiments, the 3' terminal portion and the 5' terminal portion flank the sequence having at least 50% identity to the sequence of a probe. In some embodiments where there is a 3' terminal portion, the 3' terminus may further comprise an "overhang" portion of one, two or three nucleotides which does not hybridize to a complementary nucleotide on the 5' terminal portion. In some embodiments where there is a 5' terminal portion, the 5' terminus may further comprise an "overhang" portion of one, two or three nucleotides which does not hybridize to a complementary nucleotide on the 3' terminal portion. In some embodiments, the overhang portion is one nucleotide in length.

For the purpose of this invention, in order to determine the percent identity of two sequences (such as two polynucle-otide or two polypeptide sequences), the sequences may be aligned for optimal comparison purposes (e.g., gaps can be introduced in a first sequence for optimal alignment with a second sequence). The nucleotide residues at nucleotide positions may then be compared. When a position in the first sequence is occupied by the same nucleotide residue as the corresponding position in the second sequence, then the nucleotides are identical at that position. The percent iden-tity between the two sequences is a function of the number of identical positions shared by the sequences (i.e., % identity=number of identical positions/total number of posi-tions in the reference sequence×100).

The skilled person is aware of different computer pro-grams that are available to determine the homology or identity between two sequences. For instance, a comparison of sequences and determination of percent identity between two sequences can be accomplished using a mathematical algorithm. In an embodiment, the percent identity between two amino acid or nucleic acid sequences is determined using the Needleman and Wunsch (1970) algorithm which has been incorporated into the GAP program in the Accelrys GCG software package (available online), using either a Blosum 62 matrix or a PAM250 matrix, and a gap weight of 16, 14, 12, 10, 8, 6, or 4 and a length weight of 1, 2, 3, 4, 5, or 6.

The terms "complementarity" and "complementary" are interchangeable and refer to the ability of polynucleotides to form base pairs with one another. Base pairs are typically formed by hydrogen bonds between nucleotide units in antiparallel polynucleotide strands or regions.

Complementary polynucleotide strands or regions can base pair in the Watson-Crick manner (e.g., A to T, A to U, C to G). 100% complementarity refers to the situation in which each nucleotide unit of one polynucleotide strand or region can hydrogen bond with each nucleotide unit of a second polynucleotide strand or region of equal length.

The term "probe" as used herein refers to synthetic or biologically produced nucleic acids (DNA or RNA) which, by design or selection, contain specific nucleotide sequences that allow them to hybridize, under defined stringencies, specifically (i.e., preferentially) to target nucleic acid sequences. Thus, probes may also be used interchangeably with "oligonucleotide probe". In the present teachings, probes may be labelled, e.g. with a reporter label such as a fluorophore or a quencher label. In some embodiments, probes may also comprise at least a pair of labels, compris-ing a reporter label such as a fluorophore and a quencher label, whereby the quencher label is able to attenuate the emission of the reporter label. The reporter label may be located at a different portion of the probe compared to the quencher label. In some embodiments, the position of the labels is such that when free in solution, the reporter label and quencher label come into close proximity to each other such that little or no emission can be detected from the reporter label.

In some embodiments, the one or more probe(s) may comprise a sequence which hybridizes to the complement of the tag sequence of an oligonucleotide primer. The sequence which hybridizes to the complement of the tag sequence of an oligonucleotide primer may have at least 60%, 70%, 80%, 90%, 95%, 98% or 99% identity to the tag sequence of the oligonucleotide primer. In some embodiments, the one or more probe(s) comprise a sequence identical to the tag sequence of the oligonucleotide primer. In some embodi-ments, the sequence which hybridizes to the complement of the tag sequence of an oligonucleotide primer may be 10, 11, 12, 13, 14, 15, 16, 17, 18, 19, 20, 21, 22, 23, 24, 25, 26, 27, 28, 29 or 30 nucleotides in length.

In some embodiments, the probe may comprise a loop or hairpin structure. Folding the probe in this way enhances the fluorescence quenching in its native form and leads to improved signal generation when bound to the complemen-tary target sequence. In this way, the signal-to-noise ratio of the reporting system is improved. The suggested mechanism of action is that the loop structure holds the fluor and quencher in much closer proximity, so improving quench-ing. Conversely, when the probe is bound to its target, the fluor and quencher are further apart, the increased distance maximising fluorescence and therefore signal release. In such embodiments, the probe may comprise a portion at or adjacent to the 3' terminus (the 3' terminal portion) which is complementary to a portion at or adjacent to the 5' terminus (the 5' terminal portion). In free solution, the 3' terminal portion can hybridize to the 5' terminal portion and thus form a hairpin or loop structure. In some embodiments, the 3' terminal portion and the 5' terminal portion have a length of at least 4, at least 5, at least 6 or at least 7 nucleotides. In some embodiments, the 3' terminal portion and the 5' terminal portion have a length of 4-8, 5-7 or 6 nucleotides. In some embodiments, the 3' terminal portion and the 5' terminal portion have a length of 4, 5, 6, 7 or 8 nucleotides. In some embodiments, the 3' terminal portion and the 5' terminal portion have at least 50%, at least 60%, at least 70%, at least 80%, or at least 90% complementarity. In some embodiments, the 3' terminal portion and the 5' terminal portion have 100% complementarity. In other embodiments, the 3' terminal portion and the 5' terminal portion has one, two or three mismatches in their complementary region. In some embodiments, the 3' terminal portion and the 5' terminal portion flank the sequence which hybridizes to the complement of the tag sequence. In some embodiments where there is a 3' terminal portion, the 3' terminus may further comprise an "overhang" portion of one, two or three nucleotides which does not hybridize to a complementary nucleotide on the 5' terminal portion. In some embodiments where there is a 5' terminal portion, the 5' terminus may further comprise an "overhang" portion of one, two or three nucleotides which does not hybridize to a complementary nucleotide on the 3' terminal portion. In some embodiments, the overhang portion is one nucleotide in length.

In some embodiments, where the one or more enhancer oligonucleotide primers and the one or more probes have hairpin structures, the one or more enhancer oligonucleotide primers may be been configured such that the hairpin structure in the one or more enhancer oligonucleotide primers is less stable than the hairpin structure in the one or more probes. Lowering the stability of a hairpin structure can be effected through a number of different designs, e.g. by decreasing the complementary region between the 3' terminal portion and the 5' terminal portion; by introducing mismatches in the complementary region between the 3' terminal portion and the 5' terminal portion; introducing an overhang in the 3' or 5' terminus.

The term "reporter label" as used herein should be understood to mean a molecule that is capable of emitting a detectable signal and is capable of being quenched by the quencher molecule. Examples of reporter molecules include molecules that are detectable by spectroscopic, photochemical, biochemical, immunochemical, or chemical means. Examples of reporter labels that may be employed include enzymes, enzyme substrates, radioactive atoms, fluorescent dyes, chromophores, chemiluminescent labels, or ligands having specific binding partners.

In one embodiment, the reporter label may be detectable by spectroscopy, and can be a fluorescent dye. The fluorophores for the labelled oligonucleotide pairs may be selected so as to be from a similar chemical family or a different one, such as cyanine dyes, xanthenes or the like. Fluorophores of interest include, but are not limited to fluorescein dyes (e.g. 5-carboxyfluorescein (5-FAM), 6-carboxyfluorescein (6-FAM), 2',4',1,4,-tetrachlorofluorescein (TET), 2',4',5',7', 1,4-hexachlorofluorescein (HEX), and 2'7"-dimethoxy-4', 5'dichloro-6-carboxyfluorescein (JOE)), cyanine dyes such as Cy5, dansyl derivatives, rhodamine dyes (e.g. tetramethyl-6-carboxyrhodamine (TAMRA), and tetrapropano-6-carboxyrhodamine (ROX)), DABSYL, DABCYL, cyanine, such as Cy3, anthraquinone, nitrothiazole, and nitroimidazole compounds, or other non-intercalating dyes. The term "quencher label" should be understood to a "quenching group", i.e. any fluorescence-modifying chemical group that can attenuate at least partly the light emitted by a fluorescent group. We refer herein to this attenuation as "quenching".

Hence, illumination of the fluorescent group in the close proximity of a quenching group can lead to an emission signal that is less intense than expected, or even completely absent. Quenching occurs through energy transfer between the fluorescent group and the quenching group.

In embodiments of the present invention where the probe comprises both a reporter label such as a fluorophore and a quencher label, the labels are generally positioned such that when free in solution, the reporter label and quencher label come into close proximity to each other such that little or no emission can be detected from the reporter label. This may be, for example, due to the formation of secondary structure due to the sequence of the oligonucleotide probe. In such embodiments, binding of the probes to their respective tag sequences can separate the reporter label and the quencher label such that the level of attenuation from the quencher label is decreased when compared to the probe being free in solution. In other words, binding of the probe to the tag sequence should increase emission from the reporter label on the probe. In one example, this can be by positioning the reporter label and quencher label at opposing ends or end portions of a probe. The terms "polymerase", "nucleic acid polymerase" and are used herein in a broad sense and refers to any polypeptide that can catalyse the 5'-to-3' extension of a hybridized primer by the addition of nucleotides and/or certain nucleotide analogs in a template-dependent manner. In one embodiment, the polymerase is a DNA polymerase. Non-limiting examples of DNA polymerases include RNA-dependent DNA polymerases, including without limitation, reverse transcriptases, and DNA-dependent DNA polymerases. It is to be appreciated that certain DNA polymerases (for example, but not limited to certain eubacterial Type A DNA polymerases and Taq DNA polymerase) may further comprise a structure-specific nuclease activity and that when an amplification reaction comprises an invasive cleavage reaction.

In some embodiments, the polymerase may be a modified polymerase. Polymerases can be modified in their structure either through genetic engineering (i.e. through known molecular biological techniques) or through chemical modification in order to confer certain properties. In other words, a modified polymerase as used herein refers to a polymerase, for example a DNA polymerase which has one or more of: a different primary structure (i.e. amino acid sequence), a different secondary structure, a different tertiary structure or a different quaternary structure to the one or more polymerase/s or fragments thereof, from which it is derived. As referred to above the term modified polymerase also includes within its scope fragments, derivatives and homologues of a modified polymerase as herein defined so long as it retains its polymerase function and modified properties as defined herein.

In some embodiments, the polymerase used may be a polymerase modified to attenuate or completely remove its 5'-3' exonuclease activity under the conditions used for the polymerisation reaction.

In some embodiments, the polymerase used may be a polymerase modified to be a "hot-start" polymerase. Hot-start polymerases are well known in the art as polymerases which have been modified such that they are completely inactivated at lower temperatures. During a PCR reaction when the temperature is generally increased to >90° C., the modification is reversed and the polymerase becomes active again. This technique allows to reduce non-specific amplification, particularly before the start of a PCR reaction.

Comprising in the context of the present specification is intended to meaning including.

Where technically appropriate, embodiments of the invention may be combined. Embodiments are described herein as comprising certain features/elements. The disclosure also extends to separate embodiments consisting or consisting essentially of said features/elements.

The invention will now be described with reference to the following examples, which are merely illustrative and should not in any way be construed as limiting the scope of the present invention.

EXAMPLES

Example 1: Endpoint Fluorescence Detection for a Single Nucleotide Polymorphic Assay

Abbreviations

FAM: 6-carboxy Fluorescein
HEX: 2',4', 5',7', 1,4-Hexachlorofluorescein
IABkFQ: Iowa Black® FQ
ROX: 5,6-carboxy-X-rhodamine, SE The system utilises three unlabelled oligonucleotide primers and two dual-labelled probes. The sequences of the primers and probes can be found below:

```
Allele-specific Primer 1:
                              (SEQ ID NO: 1)
5'-GAAGGTGACCAAGTTCATGCTGAAGCTCCACAATTTGGTGAATTATC

AAT-3'

Allele-specific Primer 2:
                              (SEQ ID NO: 2)
5'-GAAGGTCGGAGTCAACGGATTGAAGCTCCACAATTTGGTGAATTATC

AAA-3'

Reverse Primer:
                              (SEQ ID NO: 3)
5'-CACTCTAGTACTATATCTGTCACATGGTA-3'

FAM Probe:
                              (SEQ ID NO: 4)
5'-/6-FAM/GAAGGTGACCAAGTTCATGCT/IABkFQ/-3'

HEX Probe:
                              (SEQ ID NO: 5)
5'-/HEX/GAAGGTCGGAGTCAACGGATT/IABkFQ/-3'
```

The Sequence of FAM-labelled probe is identical to the universal tag part of the allele-specific primer 1 and the sequence of HEX labelled probe is identical to tag part of the allele-specific primer 2.

All oligonucleotides were diluted to 100 μM initial concentration using Te buffer (10 mM TRIS pH8.3 with 0.1 mM EDTA).

A 2× genotyping master mix including assay primers was created which included the following components:
1. 0.33 μM Allele-specific Primer 1
2. 0.33 μM Allele-specific Primer 2
3. 0.83 μM Reverse Primer
4. 400 nM FAM Probe
5. 400 nM HEX Probe
6. 10 mM TRIS pH 8.3
7. 100 mM KCl
8. 4.4 mM Magnesium Chloride
9. 300 μM dNTPs
10. 300 nM 5,6-carboxy-X-rhodamine, SE (5,6-ROX, SE, mixed isomer)
11. 0.05% Igepal
12. 10% Glycerol 13. 50-100 Units/mL N-terminally-truncated Taq Polymerase The genotyping assay was performed on a clear 384 well PCR plate using 4 μl final reaction volume. To the wells of the PCR plate, 41 of Genomic DNA from various Caucasian individuals at final concentration of 2 ng/μl was added. Addition of DNA was followed by the addition of 2× genotyping master mix (described above). The PCR plate was sealed using StarSeal Advanced Polyolefin Film. The plate was then thermally cycled on Peltier thermal cycler MJ PTC-200 using the following thermal cycling conditions:

| Step | Description | Temperature | Time | # Cycles |
|---|---|---|---|---|
| 1 | Enzyme activation | 94° C. | 15 min | 1 |
| 2 | Template denaturation | 94° C. | 20 secs | 10 |
| | Annealing and extension | 65-57° C. | 60 secs (drop 0.8° C. per cycle) | |
| 3 | Denaturation | 94° C. | 20 secs | 30 |
| | Annealing and extension | 57° C. | 60 secs | |

Figure 3:
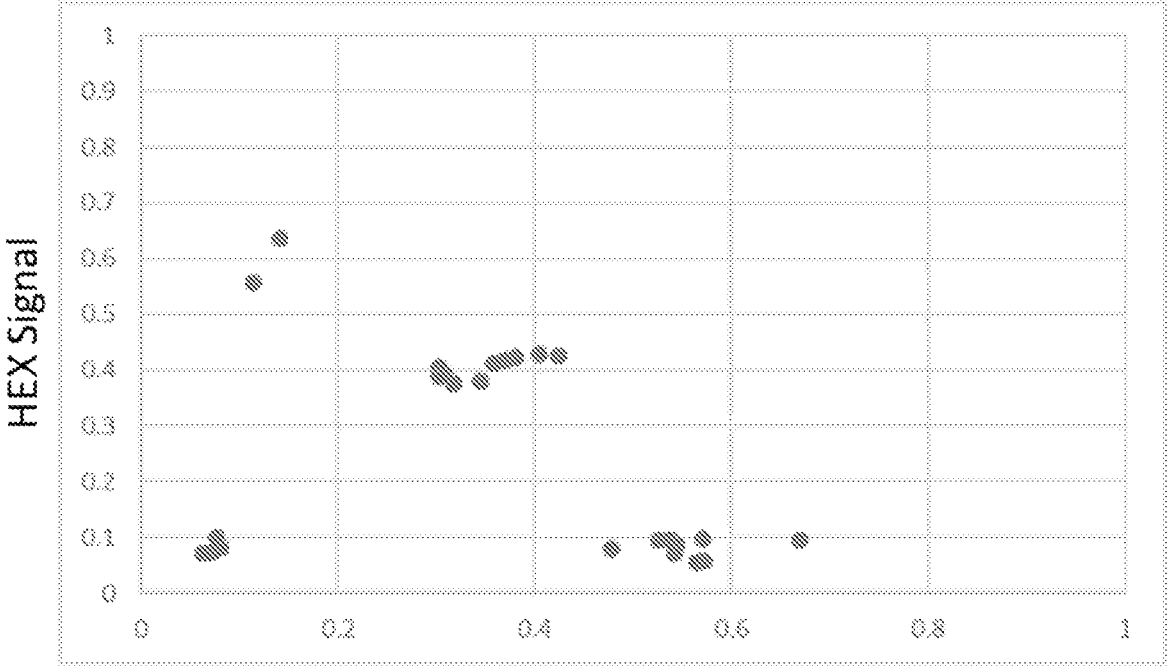
FIG. 3—Data showing the endpoint fluorescence detection for a Single Nucleotide Polymorphic assay. The assay system utilises three unlabelled oligonucleotide primers (two allele-specific primers and one universal reverse primer) and two dual-labelled probes. The sequences of the primers and probes can be found in Example 1. The data obtained was then plotted as FAM signal divided by ROX on the X-axis, and HEX signal divided by ROX on the Y-axis (the signals are normalised by ROX). Three discernible groups associated with respective genotypes were observed.

After thermal-cycling, endpoint fluorescence was recorded using Tecan Infinite F200 fluorescent plate reader, using the following wavelengths:
FAM excitation: 485 nm, FAM Emission: 520 nm
HEX excitation: 535 nm, HEX Emission: 556 nm
ROX excitation: 575 nm, ROX Emission: 610 nm The data obtained was then plotted as FAM signal divided by ROX on the X-axis, and HEX signal divided by ROX on the Y-axis. Three clearly discernible groups associated with respective genotypes were observed (FIG. 3).

Example 2: Effect of Enhancer Primer Type 1 (Single Length Universal Tag)

This example demonstrates the increased signal generation and genotyping clustering in the presence of Enhancer Primer Type 1.

As for Example 1, a protocol was used to demonstrate the importance of addition of enhancer primer on the PCR-based endpoint fluorescent SNP genotyping detection system. SNP genotyping was performed in the presence of enhancer primer type 1. A pair of enhancer primers, one for each allele was added to the 2× concentrate genotyping master mix at a final concentration of 80 nM.

```
Enhancer Primer 1:
                              (SEQ ID NO: 6)
5'-GAAGGTGACCAAGTTCATGCT-3'

Enhancer Primer 2:
                              (SEQ ID NO: 7)
5'-GAAGGTCGGAGTCAACGGATT-3'
```

Figure 4:
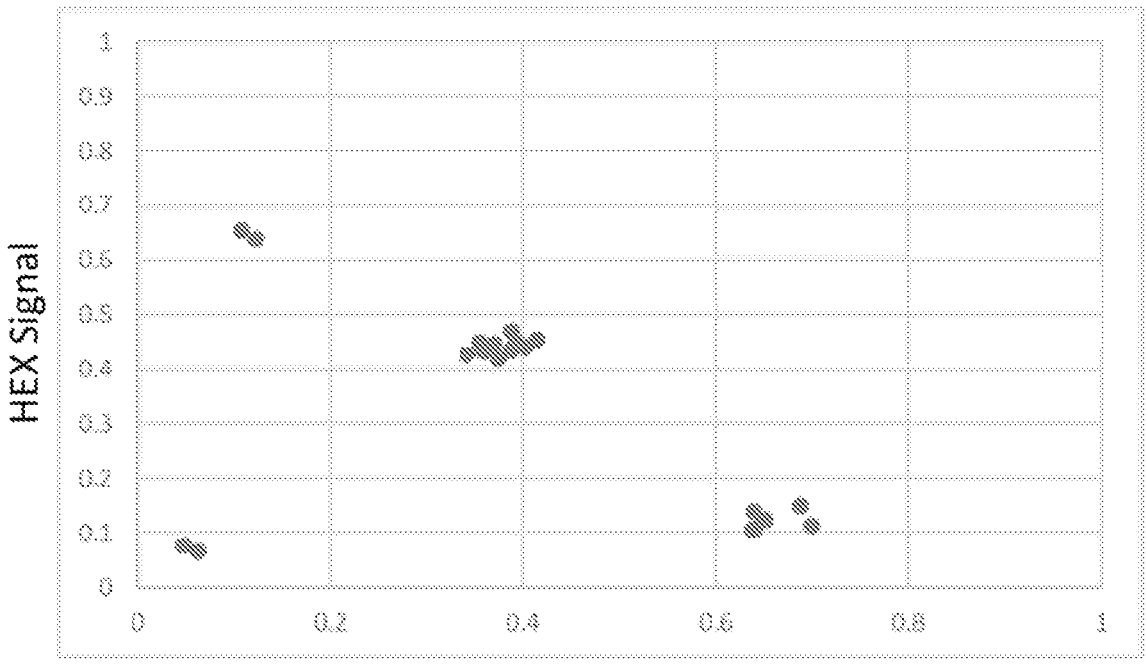
FIG. 4—Data showing effect of an enhancer primer. The assay system utilises three unlabelled oligonucleotide primers and two dual-labelled probes. The sequences of the primers and probes can be found are the same as those from Example 1 and FIG. 2, but with the addition of two enhancer primers (one for each probe/allele) as described in Example 2. The data obtained was then plotted as FAM signal divided by ROX on the X-axis, and HEX signal divided by ROX on the Y-axis (the signals are normalised by ROX). Three discernible groups associated with respective genotypes were observed.

Endpoint genotyping cluster plot clearly demonstrated increased signal to noise ratio, tighter clusters and enhanced amplification in the presence of enhancer primer. (FIG. 4)

Example 3: Effect of Enhancer Primer Type 2 (Duplicated Universal Tag)

As for Example 2, a protocol was used to demonstrate the importance of addition of enhancer primer type 2 on the PCR based endpoint fluorescent SNP genotyping detection system. SNP genotyping was performed in the presence of Enhancer Primer type 2. A pair of enhancer primers, one for each allele, was added to the 2× genotyping master mix at a final concentration of 80 nM.

```
Enhancer Primer 3:
                                    (SEQ ID NO: 8)
5'-GAAGGTGACCAAGTTCATGCTGAAGGTGACCAAGTTCATGCT-3'

Enhancer Primer 4:
                                    (SEQ ID NO: 9)
5'-GAAGGTCGGAGTCAACGGATTGAAGGTCGGAGTCAACGGATT-3'
```

Figure 5:
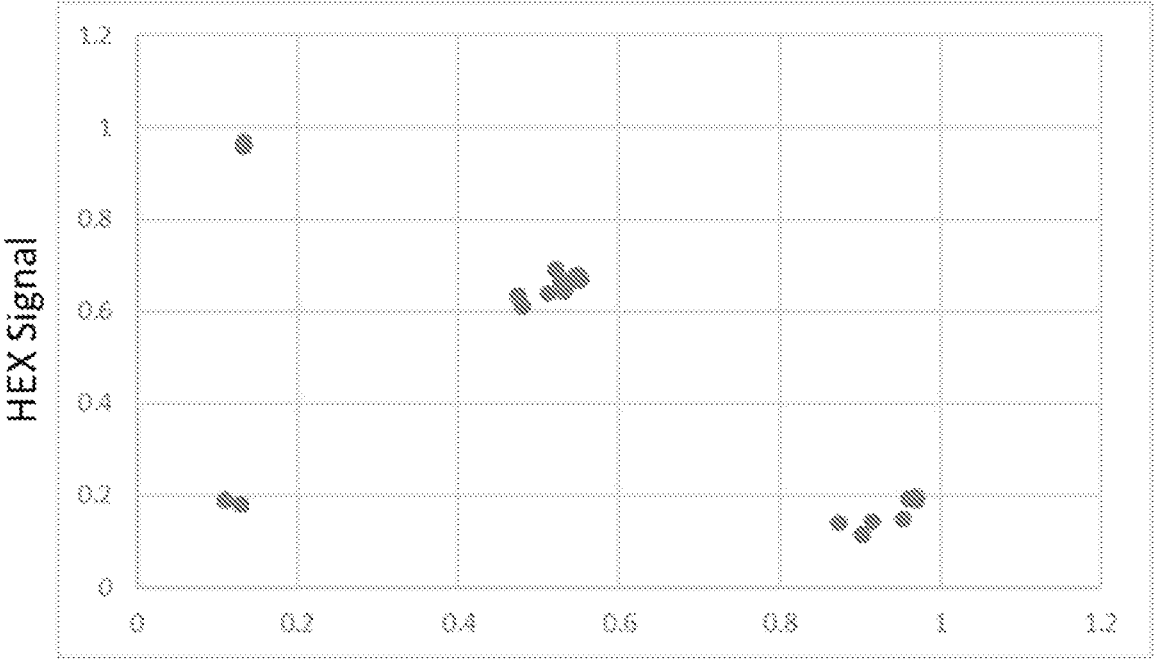
FIG. 5—Data showing effect of another type of enhancer primer. The assay system utilises three unlabelled oligonucleotide primers and two dual-labelled probes. The sequences of the primers and probes can be found are the same as those from Example 1 and FIG. 2, but with the addition of two enhancer primers (one for each probe/allele) as described in Example 3. These enhancer primers use a duplicated sequence when compared to Example 2. The data obtained was then plotted as FAM signal divided by ROX on the X-axis, and HEX signal divided by ROX on the Y-axis (the signals are normalised by ROX). Three discernible groups associated with respective genotypes were observed.

Three clearly discernible groups associated with respective genotypes were observed (FIG. 5).

Example 4: Realtime Detection of PCR Product

Realtime PCR was performed using the protocol described above (Example 1-3) to demonstrate the ability of the system to detect fluorescence in real-time at each PCR cycle.

Human DNA samples were tested in a serial dilution of 1:10 with a starting concentration of 20 ng/μl. Detection was performed only in the FAM channel using following primers and probes.

```
Allele-specific Forward Primer:
                                   (SEQ ID NO: 10)
5'-GAAGGTGACCAAGTTCATGCTGAGTGCAGGTTCAGACGTCC-3'

Reverse Primer:
                                   (SEQ ID NO: 11)
5'-CTCCCTTCCACCTCCGTACCAT-3'

FAM Probe:
                                    (SEQ ID NO: 4)
5'/6-FAM/GAAGGTGACCAAGTTCATGCT/IABkFQ/-3'

Enhancer Primer 1:
                                    (SEQ ID NO: 6)
5'-GAAGGTGACCAAGTTCATGCT-3'
```

All oligonucleotides were diluted to 100 μM initial concentration using Te buffer (10 mM TRIS pH8.3 with 0.1 mM EDTA).

A 2× genotyping master mix including assay primers was created which included the following components:
1. 0.33 μM Allele-specific Forward Primer
2. 0.83 μM Reverse Primer
3. 400 nM FAM Probe
4. 80 nM Enhancer Primer type 1
5. 10 mM TRIS pH 8.3
6. 100 mM KCl
7. 4.4 mM Magnesium Chloride
8. 300 μM dNTPs
9. 1000 nM 5,6-carboxy-X-rhodamine, SE (5,6-ROX, SE, mixed isomer)
10. 0.05% Igepal
11. 10% Glycerol
12. 20 mM TMAC
13. 50-100 Units/mL N-terminal truncated Taq Polymerase PCR was performed on a clear 384 well PCR plate using 10 μl final reaction volume. To the wells of the PCR plate, 5 μl of Genomic DNA was added with a starting concentration of 20 ng/ul to 0.02 ng/ul. Addition of DNA was followed by the addition of 2× genotyping master mix (described above). The PCR plate was sealed using StarSeal Advanced Polyolefin Film.

The plate was then thermal cycled on Applied Biosystem 7900 using following thermal cycling conditions:

| Step | Description | Temperature | Time | # Cycles |
|---|---|---|---|---|
| 1 | Enzyme activation | 94° C. | 15 min | 1 |
| 2 | Template denaturation | 94° C. | 20 secs | 10 |
| | Annealing and extension | 65-57° C. | 60 secs (drop 0.8° C. per cycle) | |
| 3 | Denaturation | 94° C. | 20 secs | 35 |
| | Annealing and extension | 57° C. | 60 secs | |

Figure 6:
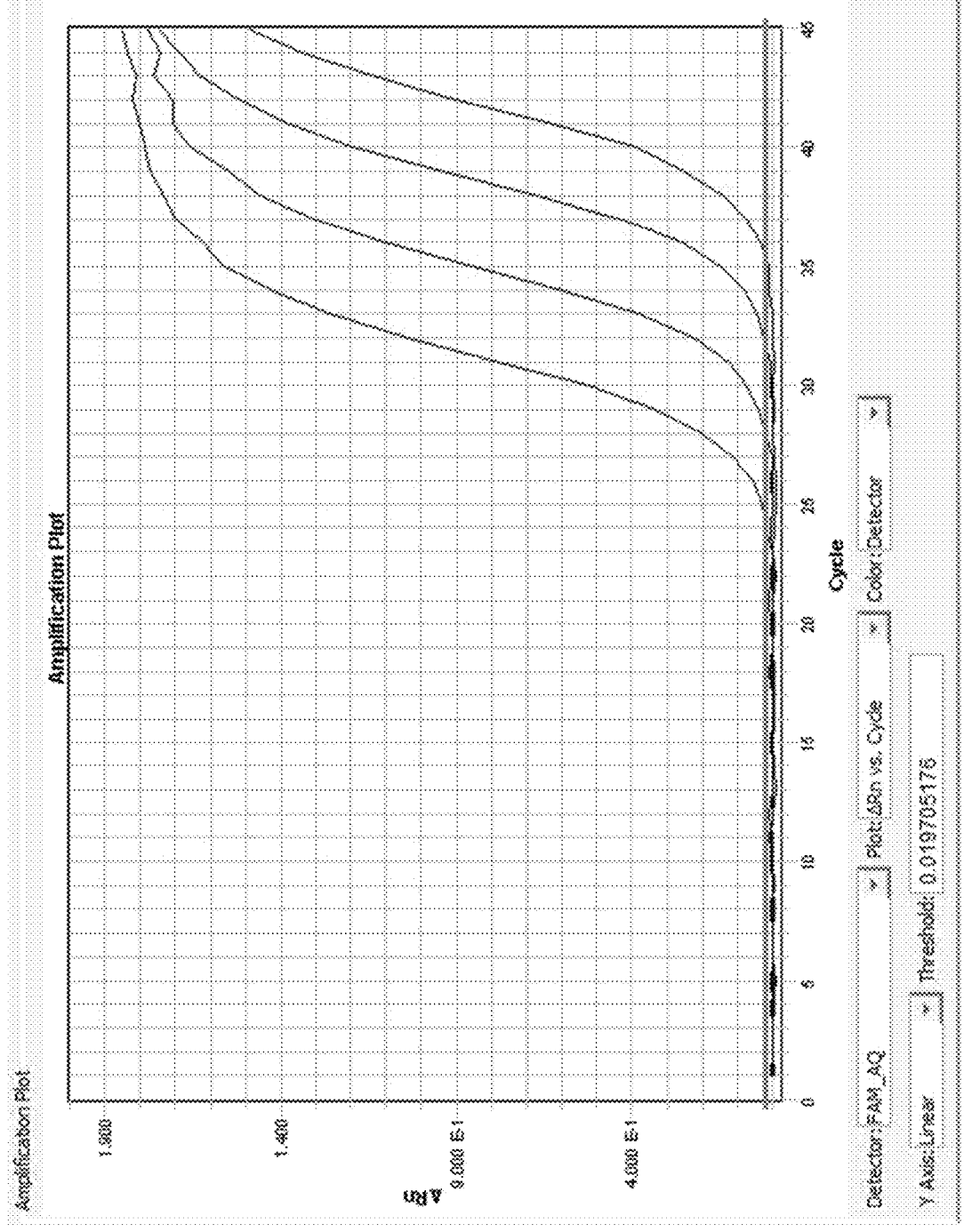
FIG. 6—Real time UPDS signal detection.

Fluorescence was recorded in real-time at each PCR cycle during annealing and extension step. Resulting data was plotted as deltaRn vs cycle and Cq values were calculated automatically using ABI 7900 software, as shown below and in FIG. 6.

| Sample Conc (ng/μL) | Cq Values |
|---|---|
| 20 | 24.0 |
| 2 | 27.2 |
| 0.2 | 30.4 |
| 0.02 | 34.0 |

This demonstrates the ability of the system to detect fluorescence in real-time.

Example 5: Use of Terminally-Truncated Taq Polymerase with Dual-Labelled Probes This example demonstrates the ability of N-terminally-deleted Taq Polymerase to release fluorescence from a quenched dual-labelled probe without the use of 5' nuclease activity of the full length Taq Polymerase.

SNP genotyping assay was performed using human genomic DNA.

```
Allele-specific Primer 1:
                                   (SEQ ID NO: 10)
5'-GAAGGTGACCAAGTTCATGCTGAGTGCAGGTTCAGACGTCC-3'

Allele-specific Primer 2:
                                   (SEQ ID NO: 12)
5'-GAAGGTCGGAGTCAACGGATTCTGAGTGCAGGTTCAGACGTCT-3'

Reverse Primer:
                                   (SEQ ID NO: 11)
5'-CTCCCTTCCACCTCCGTACCAT-3'

FAM Probe:
                                    (SEQ ID NO: 4)
5'-/6-FAM/GAAGGTGACCAAGTTCATGCT/IABkFQ/-3'

HEX Probe:
                                    (SEQ ID NO: 5)
5'-/HEX/GAAGGTCGGAGTCAACGGATT/IABkFQ/-3'
```

All oligonucleotides were diluted to 100 μM initial concentration using Te buffer (10 mM TRIS pH8.3 with 0.1 mM EDTA).

A 2× genotyping master mix including assay primers was created which included the following components:
1. 0.33 μM Allele-specific Primer 1
2. 0.33 μM Allele-specific Primer 2
3. 0.83 μM Reverse Primer
4. 400 nM FAM Probe 5. 400 nM HEX Probe 6. 10 mM TRIS pH 8.3

7. 100 mM KCl 8. 4.4 mM Magnesium Chloride 9. 300 μM dNTPs 10. 300 nM 5,6-carboxy-X-rhodamine, SE (5,6-ROX, SE, mixed isomer)

11. 0.05% Igepal 12. 10% Glycerol 13. 20 mM TMAC 14. 50-100 Units/mL N-terminally-truncated Taq Polymerase The genotyping assay was performed in a clear 384-well PCR plate using 4 μl final reaction volume. To the wells of the PCR plate, 41 of Genomic DNA from various Caucasian individuals at final concentration of 2 ng/μl was added. Addition of DNA was followed by the addition of 2× genotyping master mix (described above). The PCR plate was sealed using StarSeal Advanced Polyolefin Film. The plate was then thermally-cycled on MJ PTC-200 Peltier thermal cycler using the following thermal cycling conditions:

| Step | Description | Temperature | Time | # Cycles |
|------|-------------|-------------|------|----------|
| 1 | Enzyme activation | 94° C. | 15 min | 1 |

-continued

| Step | Description | Temperature | Time | # Cycles |
|------|-------------|-------------|------|----------|
| 2 | Template denaturation | 94° C. | 20 secs | 10 |
| | Annealing and extension | 65-57° C. | 60 secs (drop 0.8° C. per cycle) | |
| 3 | Denaturation | 94° C. | 20 secs | 30 |
| | Annealing and extension | 57° C. | 60 secs | |

After thermal-cycling, endpoint fluorescence was recorded using Tecan Infinite F200 fluorescent plate reader using the following wavelengths:

FAM excitation: 485 nm, FAM Emission: 520 nm

HEX excitation: 535 nm, HEX Emission: 556 nm

ROX excitation: 575 nm, ROX Emission: 610 nm

Figure 7:
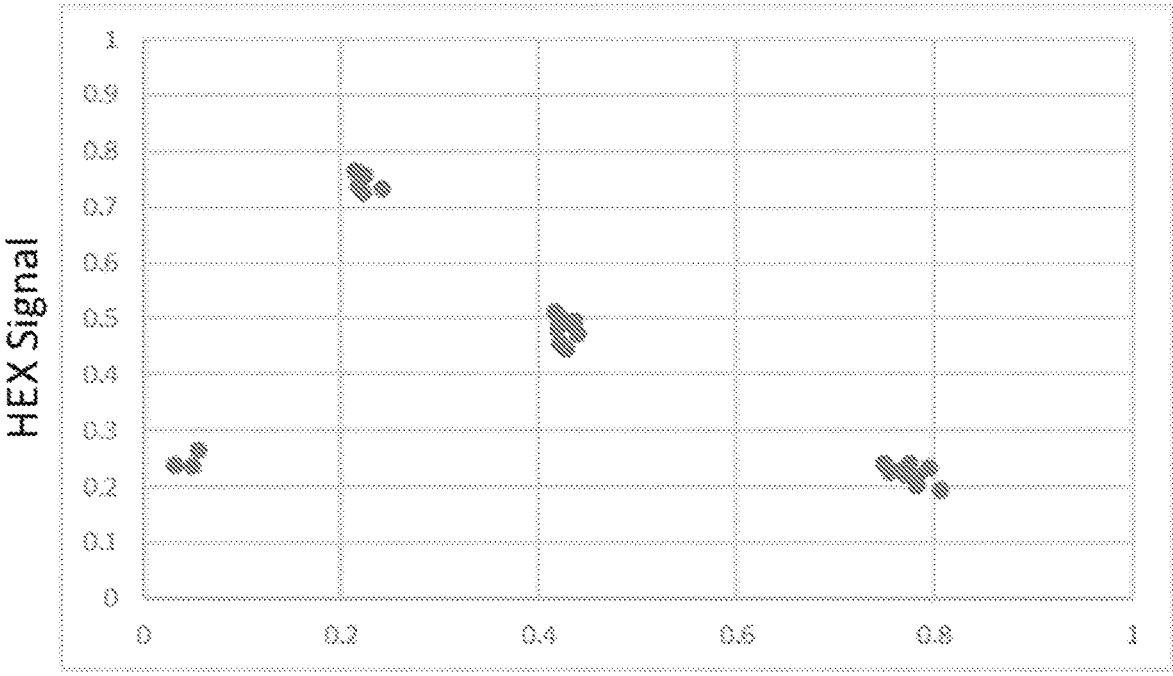
FIG. 7—Data showing the effect of using a truncated Taq polymerase with reduced 5'-3' exonuclease activity in the UPDS protocol. The assay system utilises three unlabelled oligonucleotide primers and two dual-labelled probes. The sequences of the primers and probes can be found in Example 5. The data obtained was then plotted as FAM signal divided by ROX on the X-axis, and HEX signal divided by ROX on the Y-axis (the signals are normalised by ROX). Three discernible groups associated with respective genotypes were observed.

The data obtained was then plotted as FAM signal divided by ROX on the X axis, and HEX signal divided by ROX on the Y axis. Three clearly discernible groups associated with respective genotypes were observed (FIG. 7).

Example 6: Use of Probes and Enhancer Primers with Self-Complimentary Ends

A genotyping assay according to the present invention was performed using human genomic DNA, with the use of probes and enhancer primers with self-complimentary ends forming internal hairpin/loop structures.

```
Assay Sequence
                                        (SEQ ID NO: 13)
TGTCTAGCTAGCTAGCCTTCCATCAGCCATCTTCTTTTTTCATTGTCAGTGCCT

CTTTATGAAGGTAAAATTGACATACCAGAACATATCCTCATTTTAGGCACACA

TTTCATGATTTAAGTAAATTTATACAGTTGTGCAACCATCAGCATAATCTAGT

TTTAGAACACTTCTGTTACCCTAAGCACGTTCTCCTCATA[C/T]CGTTTGTCGTC

AATCCCTACCACGGCTACCAGTCTCAGGCAGCTACTAATCTATCTGCTTTTTTT

CTGTGTAATTTTGCCTTTTCCAGAAAGTCTTTATAGATAGAAGTATACAATGT

ATAGTCTCTTCTGTTTGGCTTCTTTCATTAGAATGGTGCTTTTGAGATTCATCT

ATGTTGTGGCATGTATCAGTAGGTTGTT

Allele specific Primer 1:
                                        (SEQ ID NO: 14)
5'-AGCTGCTATTGTTACCAGTGACGCAGCTCCCTAAGCACGTTCTCCTCATAC-3'

Allele specific Primer 2:
                                        (SEQ ID NO: 15)
5'-TGGCCAGTGTATTCTGCACAGGTGGCCAACCCTAAGCACGTTCTCCTCATAT-3'

Reverse Primer:
                                        (SEQ ID NO: 16)
5'-GACTGGTAGCCGTGGTAGGGAT-3'

FAM Probe:
                                        (SEQ ID NO: 17)
5'-/6-FAM/AGCTGCTATTGTTACCAGTGACGCAGCT/IABkFQ/-3'

HEX Probe:
                                        (SEQ ID NO: 18)
5'-/HEX/TGGCCAGTGTATTCTGCACAGGTGGCCA/IABkFQ/-3'

Enhancer Primer A1:
                                        (SEQ ID NO: 19)
5'-GCTGCTATTGTTACCAGTGACGCAGCT-3'

Enhancer Primer A2:
                                        (SEQ ID NO: 20)
5'-GGCCAGTGTATTCTGCACAGGTGGCCA-3'
```

The predicted hairpin structure for the probes and enhancers are shown in FIG. 8.

All oligonucleotides were diluted to 100 µM initial concentration using TE (10 mM TRIS pH8.3 with 0.1 mM EDTA).

A 2× genotyping master mix including assay primers was created which included the following components:

1. 0.33 µM Allele Specific Primer 1
2. 0.33 µM Allele Specific Primer 2
3. 0.83 µM Reverse Primer
4. 600 nM FAM Probe
5. 600 nM HEX Probe
6. 10 mM TRIS pH 8.3
7. 100 mM KCl
8. 4.4 mM Magnesium Chloride
9. 300 µM dNTPs
10. 300 nM 5,6-carboxy-X-rhodamine, SE (5,6-ROX, SE, mixed isomer)
11. 0.05% Igepal
12. 10% Glycerol
13. 20 mM TMAC
14. 50-100 Units/mL N-terminal truncated Taq Polymerase A pair of enhancer primers, one for each allele was added to the 2× genotyping master mix at a final concentration of 80 nM.

Genotyping assay was performed on a clear 384 well PCR plate using 4 µl final reaction volume. To the wells of the PCR plate, 41 of Genomic DNA from various Caucasian individuals at final concentration of 2 ng/µl was added. Addition of DNA was followed by the addition of 2× genotyping master mix (described above). The PCR plate was sealed using Star Seal Advanced Polyolefin Film. The plate was then thermal cycled on Peltier thermal cycler MJ PTC-200 using following thermal cycling conditions:

| Step | Description | Temperature | Time | # Cycles |
|---|---|---|---|---|
| 1 | Enzyme activation | 94° C. | 15 min | 1 |
| 2 | Template denaturation | 94° C. | 20 secs | 10 |
| | Annealing and extension | 65-57° C. | 60 secs (drop 0.8° C. per cycle) | |
| 3 | Denaturation | 94° C. | 20 secs | 30 |
| | Annealing and extension | 57° C. | 60 secs | |

Post thermal-cycling endpoint fluorescence was recorded using Tecan Infinite F200 fluorescent plate reader.

FAM excitation: 485 nm, FAM Emission: 520 nm

HEX excitation: 535 nm, HEX Emission: 556 nm

ROX excitation: 575 nm, ROX Emission: 610 nm

The data obtained was then plotted as FAM signal divided by ROX on the X axis, and HEX signal divided by ROX on the Y axis, and shown in FIG. 9B. Data generated with standard probes and enhancer primer (no self-complementary ends) targeting the same SNP is shown in 9A. Improved signal to noise ratio and group divergence can be observed with the usage of probes and enhancer primers with self-complementary ends.

It will of course be understood that, although the present invention has been described by way of example, the examples are in no way meant to be limiting, and modifications can be made within the scope of the claims hereinafter. Preferred features of each embodiment of the invention are as for each of the other embodiments mutatis mutandis. All publications, including but not limited to patents and patent applications, cited in this specification are herein incorporated by reference as if each individual publication was specifically and individually indicated to be incorporated by reference herein.

The invention claimed is:

1. A method for detecting one or more target sequences in a sample by amplification, the method comprising:

a) providing an aqueous composition comprising:

i) one or more forward oligonucleotide primers having a 5' region which is a tag sequence and a 3' region specific for a target sequence;

ii) a reverse oligonucleotide primer, such that a forward oligonucleotide primer from the one or more forward oligonucleotide primers and the reverse primer operably form a primer pair;

iii) one or more probes having a reporter label and a quencher label, each of the one or more probes comprising a sequence having at least 90% identity to the tag sequence of the forward oligonucleotide primer from the one or more forward oligonucleotide primers; and iv) one or more enhancer oligonucleotide primers comprising a sequence having at least 90% identity to the sequence of a probe from the one or more probes;

b) incubating the primers and the probes with the sample and at least a DNA polymerase, wherein the DNA polymerase is a 5' nuclease-deleted DNA polymerase; and c) performing polymerase chain reaction (PCR) in a single reaction master mix comprising the sample to generate tagged nucleic acids, whereby the probes can bind to the tagged nucleic acids and label the one or more target sequences by generating a signal; wherein the reporter label is detectable spectroscopically, photochemically, biochemically, immunochemically, or chemically and is selected from the group consisting of an enzyme, enzyme substrate, radioactive atom, fluorescent dye, chromophore, chemiluminescent label, and a ligand having a specific binding partner or partners.

2. The method according to claim 1, wherein the one or more enhancer oligonucleotide primers comprise at least two distinct regions, each of the two distinct regions comprising a sequence having at least 90% identity to a sequence of the one or more probes.

3. The method according to claim 2, wherein the two distinct regions are separated by a linker region.

4. The method according to claim 3, wherein the linker region is 1 to 10 or 2 to 5 oligonucleotides in length.

5. The method according to claim 1, wherein the sequence having at least 90% identity to the tag sequence of the forward oligonucleotide primer from the one or more oligonucleotide primers is a sequence having at least 95%, 98% or 99% identity to the tag sequence of the forward oligonucleotide primer from the one or more forward oligonucleotide primers or a sequence which is 100% identical to the tag sequence of the forward oligonucleotide primer from the one or more forward oligonucleotide primers.

6. The method according to claim 1, wherein the sequence having at least 90% identity to the tag sequence of the probe from the one or more probes is a sequence having at least 95%, 98% or 99% identity to the tag sequence of the probe from the one or more probes or a sequence which is 100% identical to the sequence of the probe from the one or more probes.

7. The method according to claim 1, wherein at least 4, 20, or 30 cycles of PCR are performed in the single reaction master mix.

8. The method according to claim 1, further comprising: d) measuring the signal generated by the binding of the probes to the tagged nucleic acids.

9. The method according to claim 8, wherein the measurement is made in real time or at the end of the reaction.

10. The method according to claim 1, wherein the composition further comprises a quaternary ammonium salt.

11. The method according to claim 10, wherein the quaternary ammonium salt is a tetramethylammonium salt, optionally wherein the tetramethylammonium salt is tetramethylammonium chloride (TMAC).

12. The method according to claim 1, wherein each of the one or more probes comprises a portion at or adjacent to its 3' terminus which is complementary to a portion at or adjacent to its 5' terminus, optionally wherein:

(a) the its 3' terminal portion and/or the its 5' terminal portion have a length of at least 4, at least 5, at least 6 or at least 7 nucleotides, and/or (b) wherein the its 3' terminal portion and the its 5' terminal portion have at least 90% or 100% complementarity.

13. The method according to claim 1, wherein each of the one or more enhancer oligonucleotide primers comprises a portion at or adjacent to its 3' terminus which is complementary to a portion at or adjacent to its 5' terminus, optionally wherein (a) the its 3' terminal portion and/or the its 5' terminal portion have a length of at least 4, at least 5, at least 6 or at least 7 nucleotides, and/or (b) wherein the its 3' terminal portion and the 5' terminal portion: (i) have at least 50%, at least 60%, at least 70%, at least 80%, or at least 90% or 100% complementarity, or (ii) comprise one, two or three mismatches.

14. The method according to claim 1, wherein:

(a) the 3' terminus or the 5' terminus of the one or more probes further comprises an overhang portion of one, two or three nucleotides which does not hybridize to nucleotides on the 5' or 3' terminal portion of the one or more probes respectively; or (b) the one or more enhancer oligonucleotide primers have a hairpin structure, the one or more probes have a hairpin structure, and the hairpin structure in the one or more enhancer oligonucleotide primers is less stable than the hairpin structure in the one or more probes.

15. The method according to claim 1, wherein the reporter label is a fluorescent dye and is detectable spectroscopically or photochemically.

16. The method according to claim 1, wherein the reporter label is an enzyme and is detectable photochemically, spectroscopically, biochemically, immunochemically, or chemically.

17. The method according to claim 1, wherein the reporter label is an enzyme substrate and is detectable photochemically, spectroscopically, biochemically, immunochemically, or chemically.

18. The method according to claim 1, wherein the reporter label is a radioactive atom and is detectable photochemically or chemically.

19. The method according to claim 1, wherein the reporter label is a chromophore and is detectable spectroscopically or photochemically.

20. The method according to claim 1, wherein the reporter label is a chemiluminescent label and is detectable spectroscopically or photochemically.

21. The method according to claim 1, wherein the reporter label is a ligand having a specific binding partner or partners and is detectable biochemically, chemically, or immunochemically.

22. A method for detecting one or more target sequences in a sample by amplification, the method comprising:

a) providing an aqueous composition comprising:

i) one or more forward oligonucleotide primers having a 5' region which is a tag sequence and a 3' region specific for a target sequence;

ii) a reverse oligonucleotide primer, such that a forward oligonucleotide primer from the one or more forward oligonucleotide primers and the reverse primer operably form a primer pair;

iii) one or more probes having a reporter label and a quencher label, each of the one or more probes comprising a sequence having at least 90% identity to the tag sequence of the forward oligonucleotide primer from the one or more forward oligonucleotide primers; and iv) one or more enhancer oligonucleotide primers comprising a sequence having at least 90% identity to the sequence of a probe from the one or more probes;

b) incubating the primers and the probes with the sample and at least a DNA polymerase, wherein the DNA polymerase is a 5' nuclease-deleted DNA polymerase; and c) performing polymerase chain reaction (PCR) in a single reaction master mix comprising the sample to generate tagged nucleic acids, whereby the probes can bind to the tagged nucleic acids and label the one or more target sequences by generating a signal;

wherein the reporter label is a fluorescent dye and is detectable spectroscopically or photochemically;

wherein the reporter label is an enzyme and is detectable photochemically, spectroscopically, biochemically, immunochemically, or chemically;

wherein the reporter label is an enzyme substrate and is detectable photochemically, spectroscopically, biochemically, immunochemically, or chemically;

wherein the reporter label is a radioactive atom and is detectable photochemically or chemically;

wherein the reporter label is a chromophore and is detectable spectroscopically or photochemically;

wherein the reporter label is a chemiluminescent label and is detectable spectroscopically or photochemically; or wherein the reporter label is a ligand having a specific binding partner or partners and is detectable biochemically, chemically, or immunochemically.

23. The method according to claim 1, further comprising increasing the signal-to-noise ratio of the signal generated in step c) by adding a quaternary ammonium salt.

24. The method according to claim 23, wherein:

(a) the quaternary ammonium salt is a tetramethylammonium salt, optionally wherein the tetramethylammonium salt is tetramethylammonium chloride (TMAC); and (b) the presence of TMAC increases the signal-to-noise ratio of the signal from the probes.

* * * * *

SEQUENCE LISTING

```
<160> NUMBER OF SEQ ID NOS: 24

<210> SEQ ID NO 1
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 1
gaaggtgacc aagttcatgc tgaagctcca caatttggtg aattatcaat          50

<210> SEQ ID NO 2
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 2
gaaggtcgga gtcaacggat tgaagctcca caatttggtg aattatcaaa          50

<210> SEQ ID NO 3
<211> LENGTH: 29
<212> TYPE: DNA
<213> ORGANISM: Artificial Sequence
<220> FEATURE:
<223> OTHER INFORMATION: Synthetic oligonucleotide
```

-continued

```
<400> SEQUENCE: 3
cactctagta ctatatctgt cacatggta                                   29

<210> SEQ ID NO 4
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<223> OTHER INFORMATION: 5' 56-FAM
<220> FEATURE:
<221> NAME/KEY: misc_feature
<223> OTHER INFORMATION: 3' 3IABkFQ

<400> SEQUENCE: 4
gaaggtgacc aagttcatgc t                                           21

<210> SEQ ID NO 5
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<223> OTHER INFORMATION: 5' 5HEX
<220> FEATURE:
<221> NAME/KEY: misc_feature
<223> OTHER INFORMATION: 3' 3IABkFQ

<400> SEQUENCE: 5
gaaggtcgga gtcaacggat t                                           21

<210> SEQ ID NO 6
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 6
gaaggtgacc aagttcatgc t                                           21

<210> SEQ ID NO 7
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 7
gaaggtcgga gtcaacggat t                                           21

<210> SEQ ID NO 8
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 8
gaaggtgacc aagttcatgc tgaaggtgac caagttcatg ct                    42

<210> SEQ ID NO 9
<211> LENGTH: 42
```

-continued

```
<212> TYPE: DNA
<213> ORGANISM: Artificial Sequence
<220> FEATURE:
<223> OTHER INFORMATION: Synthetic oligonucleotide

<400> SEQUENCE: 9
gaaggtcgga gtcaacggat tgaaggtcgg agtcaacgga tt                          42

<210> SEQ ID NO 10
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 10
gaaggtgacc aagttcatgc tgagtgcagg ttcagacgtc c                           41

<210> SEQ ID NO 11
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 11
ctcccttcca cctccgtacc at                                                22

<210> SEQ ID NO 12
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 12
gaaggtcgga gtcaacggat tctgagtgca ggttcagacg tct                         43

<210> SEQ ID NO 13
<211> LENGTH: 401
<212> TYPE: DNA
<213> ORGANISM: Homo sapiens

<400> SEQUENCE: 13
tgtctagcta gctagccttc catcagccat cttctttttt cattgtcagt gcctctttat       60
gaaggtaaaa ttgacatacc agaacatatc ctcattttag gcacacattt catgatttaa      120
gtaaatttat acagttgtgc aaccatcagc ataatctagt tttagaacac ttctgttacc      180
ctaagcacgt tctcctcata ycgtttgtcg tcaatcccta ccacggctac cagtctcagg      240
cagctactaa tctatctgct tttttctgt gtaattttgc cttttccaga aagtctttat       300
agatagaagt atacaatgta tagtctcttc tgtttggctt ctttcattag aatggtgctt      360
ttgagattca tctatgttgt ggcatgtatc agtaggttgt t                          401

<210> SEQ ID NO 14
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 14
agctgctatt gttaccagtg acgcagctcc ctaagcacgt tctcctcata c               51
```

-continued

```
<210> SEQ ID NO 15
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 15
tggccagtgt attctgcaca ggtggccaac cctaagcacg ttctcctcat at          52

<210> SEQ ID NO 16
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 16
gactggtagc cgtggtaggg at                                           22

<210> SEQ ID NO 17
<211> LENGTH: 28
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<223> OTHER INFORMATION: 5' 6-FAM
<220> FEATURE:
<221> NAME/KEY: misc_feature
<223> OTHER INFORMATION: 3' IABkFQ

<400> SEQUENCE: 17
agctgctatt gttaccagtg acgcagct                                     28

<210> SEQ ID NO 18
<211> LENGTH: 28
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<223> OTHER INFORMATION: 5' HEX
<220> FEATURE:
<221> NAME/KEY: misc_feature
<223> OTHER INFORMATION: 3' IABkFQ

<400> SEQUENCE: 18
tggccagtgt attctgcaca ggtggcca                                     28

<210> SEQ ID NO 19
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 19
gctgctattg ttaccagtga cgcagct                                      27

<210> SEQ ID NO 20
<211> LENGTH: 27
<212> TYPE: DNA
<213> ORGANISM: Artificial Sequence
<220> FEATURE:
<223> OTHER INFORMATION: Synthetic oligonucleotide
```

-continued

```
<400> SEQUENCE: 20
ggccagtgta ttctgcacag gtggcca                                           27

<210> SEQ ID NO 21
<211> LENGTH: 28
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<223> OTHER INFORMATION: 5' 6-FAM
<220> FEATURE:
<221> NAME/KEY: misc_feature
<223> OTHER INFORMATION: 3' IABkFQ

<400> SEQUENCE: 21
agctgctatt gttaccagtg acgcagct                                          28

<210> SEQ ID NO 22
<211> LENGTH: 28
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<223> OTHER INFORMATION: 5' HEX
<220> FEATURE:
<221> NAME/KEY: misc_feature
<223> OTHER INFORMATION: 3' IABkFQ

<400> SEQUENCE: 22
tggccagtgt attctgcaca ggtggcca                                          28

<210> SEQ ID NO 23
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 23
gctgctattg ttaccagtga cgcagct                                           27

<210> SEQ ID NO 24
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 24
ggccagtgta ttctgcacag gtggcca                                           27
```